United States Patent
Duffy et al.

(10) Patent No.: US 11,823,585 B2
(45) Date of Patent: Nov. 21, 2023

(54) METHODS AND SYSTEMS FOR WRITING SKILL DEVELOPMENT

(71) Applicant: SOCIETE BIC, Clichy (FR)

(72) Inventors: David Duffy, Zürich (CH); William Andrew Schnabel, Lausanne (CH); Christopher-John Wright, Lausanne (CH); Harry Michael Cronin, Lausanne (CH)

(73) Assignee: SOCIETE BIC, Clichy (FR)

( * ) Notice: Subject to any disclaimer, the term of this patent is extended or adjusted under 35 U.S.C. 154(b) by 0 days.

(21) Appl. No.: 17/675,986

(22) Filed: Feb. 18, 2022

(65) Prior Publication Data

US 2022/0309945 A1    Sep. 29, 2022

(30) Foreign Application Priority Data

Mar. 24, 2021  (EP) .................................... 21305365

(51) Int. Cl.
  *G09B 11/00* (2006.01)
  *G09B 5/06* (2006.01)
  *A61B 5/11* (2006.01)

(52) U.S. Cl.
  CPC .............. *G09B 11/00* (2013.01); *G09B 5/067* (2013.01); *A61B 5/1124* (2013.01)

(58) Field of Classification Search
  CPC .......... G09B 11/00; G09B 11/06; G09B 11/08
  See application file for complete search history.

(56) References Cited

U.S. PATENT DOCUMENTS

| 6,215,901 B1 * | 4/2001 | Schwartz | G06V 30/1423 |
| | | | 382/187 |
| 9,354,725 B2 * | 5/2016 | Al-Sharif | G06F 3/03542 |
| 9,746,939 B2 * | 8/2017 | Baek | G06F 3/0425 |
| (Continued) | | | |

FOREIGN PATENT DOCUMENTS

| WO | WO-9832107 A1 * | 7/1998 | ............. G09B 11/00 |
| WO | 2014006198 A1 | 1/2014 | |
| WO | WO-2014006198 A1 * | 1/2014 | ......... G06F 3/04883 |

OTHER PUBLICATIONS

Extended European Search Report dated Oct. 12, 2021 in counterpart European Patent Application No. 21305365.5 (12 pages, in English).

*Primary Examiner* — Robert J Utama
*Assistant Examiner* — Correll T French
(74) *Attorney, Agent, or Firm* — Bookoff McAndrews, PLLC

(57) ABSTRACT

A computer-implemented method for designing a user-specific writing skill game is provided. The computer-implemented method comprises tracking a handwriting performance and generating a digital representation of the handwriting performance. The handwriting performance is performed by a user with a writing instrument. The method further comprises identifying user-specific handwriting skills which require improvement based on the digital representation of the handwriting performance. Then a writing skill game is designed. The writing skill game is designed to include one or more game tasks to be performed by the user. The one or more game tasks require the user to apply the user-specific handwriting skills which are to be improved.

20 Claims, 5 Drawing Sheets

(56) References Cited

U.S. PATENT DOCUMENTS

| | | | |
|---|---|---|---|
| 2009/0253107 A1* | 10/2009 | Marggraff | G06F 3/0317 |
| | | | 434/165 |
| 2010/0003659 A1* | 1/2010 | Edmonds | G09B 7/04 |
| | | | 434/350 |
| 2010/0103178 A1* | 4/2010 | Song | G06F 3/03545 |
| | | | 345/473 |
| 2012/0258436 A1* | 10/2012 | Lee | G09B 19/003 |
| | | | 434/362 |
| 2013/0254660 A1 | 9/2013 | Fujioka | |
| 2015/0336421 A1* | 11/2015 | Neubauer | G09B 19/00 |
| | | | 434/335 |
| 2019/0101754 A1 | 4/2019 | Bharti et al. | |
| 2019/0369755 A1* | 12/2019 | Roper | G06F 3/0481 |

* cited by examiner

METHODS AND SYSTEMS FOR WRITING SKILL DEVELOPMENT

CROSS REFERENCE TO RELATED APPLICATIONS

This application claims priority from European patent application No. 21305365.5, filed on Mar. 24, 2021, the contents of which are hereby incorporated herein in their entirety by this reference.

TECHNICAL FIELD

The present disclosure relates to computer-implemented methods for designing a user-specific writing skill game and for practicing handwriting skills. The present disclosure further relates to systems configured to perform such computer-implemented methods.

BACKGROUND

Handwriting is viewed as involving a suite of perceptual, motor and cognitive abilities which must work in unison if unskilled users (e.g. children) are to write letters efficiently. Learning handwriting involves mastering many levels of handwriting skills such as motor skills (particularly from gross to fine motor), gaze skills or other skills. For example, children and adults, novices and experts, exhibit differences in gaze while writing. This includes inefficient gaze fixations in children, as well as reduced fluency from lack of planning. If the basic skills are not properly mastered, learners may experience problems later in their development.

Gaze training (for example, quiet eye techniques to focus on the target and not the instrument or instructing on where an expert in the field would look) has been shown to improve coordination and motor development for novices in a range of tasks. Handwriting guidance systems, which use haptic, visual, or other feedback to allow a user to repeatedly practice writing certain characters, are known in the art. However, recent research on haptic feedback in handwriting practice indicates that such simple guidance systems are not effective for learners as they encourage over-reliance on the guides. Furthermore, even if the shapes of characters are correctly reproduced (following a guidance system or otherwise), if poor technique is used during the practice this may in fact be counterproductive as it reinforces the wrong user techniques through muscle memory, which can cause problems in later development.

The object of the present disclosure is to provide alternative computer-implemented methods and systems which allow a user to identify and train deficiencies in handwriting skills.

SUMMARY

The present disclosure relates to computer-implemented methods, and a system. The computer-implemented method for designing a user-specific writing skill game comprises tracking a handwriting performance and generating a digital representation of the handwriting performance. The handwriting performance is performed by a user with a writing instrument. Particularly, the writing instrument may be a smart pen. The method further comprises identifying user-specific handwriting skills which require improvement based on the digital representation of the handwriting performance. Then a writing skill game is designed. The writing skill game is designed to include one or more game tasks to be performed by the user. The one or more game tasks require the user to apply the user-specific handwriting skills which are to be improved.

In aspects, the handwriting performance may comprise a writing performance, a drawing performance, a marking performance and/or any other pen-based activity.

In aspects, the handwriting skills may include skills and/or procedures which are required for a user to produce handwriting. In examples, the handwriting skills may not include the whole shapes or outlines of written characters. Specifically, the handwriting skills may include the underlying skills or pen motions required to create written characters.

In aspects, the handwriting skills may include gross and/or fine motor skills. In some examples, the handwriting skills may include ocular motor skills. In some examples, the handwriting skills may include eye gaze behaviour. Specifically, the handwriting skills may include correct or optimum eye gaze behaviour. In examples, the handwriting skills may include hand-eye co-ordination. In examples, the handwriting skills may include other observable physical motions or behaviours required to produce individual parts of characters or other written features. In examples, the handwriting skills, specifically the user-specific handwriting skills which require improvement, may include a combination of the above-mentioned skills. For instance, the handwriting skills may include motor skills (e.g. gross and/or fine) and eye gaze behaviour.

In aspects, tracking the handwriting performance may involve capturing via sensors input data of the handwriting performance. The input data may include motion data and/or force data. For instance, the motion data may include motion of the user (e.g. user motion) and/or motion of the writing instrument. For instance, the force data may include data regarding the force applied by the user to the writing instrument, e.g. gripping force, and/or force applied via the writing instrument to the paper (or other base onto which the handwriting is performed, e.g. a touch display). In examples, the input data may be captured via optical sensors. In examples, the input data may be captured via other position tracking techniques. In examples, the handwriting performance may be tracked via a user input tracking system.

In aspects, the input data may be used to calculate a writing instrument tip path and user techniques. In examples, the writing instrument tip path may be calculated based on tracked written characters and/or tracked user motion. In examples, the user techniques may be calculated based on tracked written characters and/or tracked user motion. In aspects, the user techniques may include implied forces and/or techniques of the user motion, e.g. start point, end point and/or course of user motion during, e.g. a written character or written word. In examples, the user techniques may include other features of the user's input to the writing instrument. In aspects, the writing instrument tip path may be calculated via dead reckoning using the input data.

In aspects, the user techniques may be measured from the input data. Additionally or alternatively, the user techniques may be acquired by comparing the captured input data with default input data. In examples, the default input data may be input data captured during a handwriting performance of another user, in particular that of an expert user.

In aspects, writing instrument tip path data and user techniques data may be generated by storing data representing the writing instrument tip path and user techniques as a function of time, respectively. Specifically, the writing instrument tip path data and user techniques data may be stored in a handwriting database.

In aspects, generating a digital representation of the handwriting performance may include identifying from the writing instrument tip path data discrete characters written by the user during the handwriting performance. The identified characters may be linked with the user techniques employed to produce them. In examples, each identified character may be stored with the respectively linked user techniques in a handwriting database.

In aspects, discrete characters may be identified by segmenting the writing instrument tip path data into time-gated periods respectively representing a discrete character. In examples, the writing instrument tip path data may be segmented by identifying a start and an end of a time-gated period based on one or more of predefined criteria. In examples, the predefined criteria may comprise changes in position or orientation of the writing instrument tip path exceeding a defined threshold. In examples, the predefined criteria may comprise temporal gaps between discrete characters. In examples, the predefined criteria may comprise manual user input. In examples, the predefined criteria may comprise other features of the writing instrument tip path data and/or user techniques data. Specifically, the predefined criteria may comprise a combination of some or all of the above-mentioned criteria, e.g. changes in position or orientation of the writing instrument tip path exceeding a defined threshold and temporal gaps between discrete characters.

In aspects, discrete characters may include text elements and/or non-text elements. In examples, discrete characters may be defined as elements which are suitably unique to be associated with a 'correct' user technique. In examples, the text elements may include letters, signs, and/or glyphs. In examples, the non-text elements may include geometric shapes and/or patterns.

In aspects, generating a digital representation of the handwriting performance may further include analyzing the writing instrument tip path data over an extended time interval larger than that of one discrete character to determine speed and/or accuracy of the handwriting performance during that extended time interval. Specifically, speed and/or accuracy of completing written sentences, written words and/or written characters may be analyzed. In examples, the accuracy and the speed of the handwriting performance may be referred to as user fluency level. In examples, the writing instrument tip path data and the user fluency level are stored in a handwriting database. In examples, the extended time interval may represent one or more words of the handwriting performance, one or more sentences of the handwriting performance and/or the whole handwriting performance.

In aspects, identifying user-specific handwriting skills which require improvement may comprise applying a handwriting skill extraction algorithm. In examples, the handwriting skill extraction algorithm may be configured to analyze the identified characters linked with the user techniques to determine handwriting skills of the user. In examples, the handwriting skill extraction algorithm may be further configured to identify one or more problem areas of the handwriting skills and to determine them as user-specific handwriting skills which require improvement.

In aspects, the handwriting skills of the user may be determined based on a comparison of the identified characters with respective ideal characters stored on an ideal techniques database. In examples, the handwriting skills may be determined at a character level. In examples, the handwriting skills may be determined by comparing writing instrument tip path data and user techniques of the identified character with respective data of the ideal character. Based on the comparison, handwriting skills used for a respective character may be determined "high" when the respective data of the identified character matches with the ideal character within a defined threshold. Based on the comparison, handwriting skills used for a respective character may be determined "low" when the respective data of the identified character does not match with the ideal character within the defined threshold. Thereby, handwriting skill levels in various handwriting skills may be determined from the user techniques and identified characters.

In aspects, handwriting skills of the user may be determined based on a comparison of the speed of writing motions, the accuracy and/or similarity of repeated characters within the writing instrument tip path of the extended time interval.

In aspects, problem areas may be identified by detecting a difference between the user technique used for an identified character and an ideal technique of an ideal character stored on the ideal techniques database. In examples, the difference may be a predefined threshold and/or a predefined constraint. In examples, the difference may be determined as the use of an upward stroke (user) technique to form part of a character when the ideal technique would be a downward stroke. Thereby, the handwriting skill extraction algorithm may provide possibilities for ranking and evaluating the handwriting skills which would be most advantageous for the user to practice.

In aspects, problem areas may be identified by detecting a difference between writing instrument tip path data of an identified character and ideal writing instrument tip path data of an ideal character stored on the ideal techniques database. In examples, a problem area of handwriting skill is calculated based on a deviation of the identified character from the ideal character.

In aspects, problem areas may be identified by examining a user fluency level and comparing it to known fluency levels from the ideal techniques database. In examples, the user fluency level is determined based on relative time to complete the handwriting performance or part of it and the resulting accuracy. Specifically, the user fluency level of the extended time interval may be compared to known fluency levels stored on the ideal techniques database.

In aspects, identified problem areas may be prioritized. In examples, only a subset, e.g. one or more, of handwriting skills from the problem areas is selected based on the prioritization to be determined as user-specific handwriting skills which require improvement. In examples, the most frequently occurring problem areas identified over several written characters and/or over several handwriting performances may be prioritized.

In aspects, designing a writing skill game may comprise applying a game design engine configured to design the writing skill game. In examples, the game design engine may be configured to incorporate one or more of the identified problem areas as game tasks into the writing skill game. In examples, the game design engine may be further configured to incorporate a positive feedback mechanism into the writing skill game. In examples, the positive feedback mechanism may be configured to output positive feedback to the user when the game tasks are performed correctly. In examples, writing skill games may be designed with varying lengths and varying required levels of commitment from the user. Thereby short games may be incorporated into small writing breaks while longer games may be played as standalone sessions. In examples, the game design engine may be configured to consider the mental or cognitive workload placed on the user when performing the writing skill game. Thereby an appropriate time to 'prompt' a user to perform the game may be determined.

In aspects, the writing skill game may be designed from scratch. In examples, the writing skill game may be designed by adapting pre-existing game level templates. In examples, the writing skill game may be designed by following basic algorithmic game design steps which allow generation of new games following certain patterns. Specifically, the patterns may be mazes or doodles.

In aspects, the writing skill game may be designed by modifying existing games such that the writing skill game includes the game tasks which require the user to apply the user-specific handwriting skills which are to be improved. In examples, the game design engine may contain or access a database of several pre-designed games or parts of games. In examples, the game design engine may be configured to modify the pre-designed games or parts of games to suit the user's handwriting skills. In examples, the game design engine may apply. generative design algorithms for the modification. In examples, existing games may be video games. In examples, existing games may be games designed specifically for use with the game design engine or unrelated games. In examples, unrelated games may be game whose level features and/or controller mappings may be externally modified. In examples, unrelated games may be game whose hardware accepts motion inputs.

In aspects, existing games may be modified by modifying the controller input mappings. In examples, the game design engine may be configured to set an optimum technique to perform an action in the game to match the ideal technique required for the identified problem areas.

In aspects, existing games may be modified by modifying the level designs of existing games, particularly racing games. In examples, the game design engine may be configured to algorithmically generate course designs for the racing game such that a user completing the course is required to perform user techniques associated with the problem areas.

In aspects, the writing skill game may be designed to comprise game tasks which allow the user to practice motor skills. In examples, the game tasks may be designed to comprise motor skills, e.g. certain ranges of motions, which can be captured via motions of the writing instrument.

In aspects the writing skill game may be designed to comprise game tasks which allow the user to practice gaze skills.

In aspects, the writing skill game may be designed to comprise game tasks which allow the user to practice the user fluency level.

In aspects, the writing skill game may be designed to comprise game tasks which allow the user to practice gross and/or fine motor skills. In examples, the writing skill game may be designed to comprise game tasks which allow the user to practice ocular motor skills. In examples, the writing skill game may be designed to comprise game tasks which allow the user to practice eye gaze behaviour, particularly correct or optimum eye gaze behaviour. In examples, the writing skill game may be designed to comprise game tasks which allow the user to practice hand-eye co-ordination. In examples, the writing skill game may be designed to comprise game tasks which allow the user to practice grip of the smart pen. In examples, the writing skill game may be designed to comprise game tasks which allow the user to practice force or speed of motion. In examples, the writing skill game may be designed to comprise game tasks which allow the user to practice other observable physical motions or behaviours required to produce individual parts of characters or other written features. The writing skill game may be designed to include one or more game tasks which allow the user to practice one or more of the above-mentioned handwriting skills.

In aspects, the game design engine may be configured to determine an appropriate level of difficulty of the writing skill game based on the handwriting skills of the user. In examples, for determining the level of difficulty, the game design engine may check the handwriting database for any previous writing skill games the user has played and the handwriting skills and/or problem areas included in those games.

In aspects, the designed writing skill game may be output via an output system. In examples the output system is a smart pen output system or an external device output system. In examples, based on the writing skill game user outputs may be calculated by the output system. In examples, the user outputs may comprise guides to the user enabling the user to play the game. The guides may include, for instance haptic feedback, projected light, and/or other guides. In examples, the user outputs may be communicated to an output device. In examples, the output device may be the writing instrument and/or to an external device, particularly a smartphone or a display. In examples, the output system may be configured to transform the writing skill game into a format useable by the external device/writing instrument (taking into account the external device's input/output hardware, graphics capabilities, required data structures), and to transmit the correctly formatted writing skill game to the external device/writing instrument.

The present disclosure further relates to a computer-implemented method for practicing handwriting via a user-specific writing skill game. The method comprises transmitting a user-specific writing skill game to an output device. Then game task performances of the writing skill game performed by a user via an input device are recorded. User motions are tracked via a user input tracking system while the user is performing the writing skill game. Feedback to the user is output via the output device. In examples, user motions may be tracked analogously to tracking of handwriting performance above.

In aspects, the writing skill game may be designed by the computer-implemented method for designing a user-specific writing skill game.

In aspects, before transmitting the writing skill game to the output device, the method may comprise any one of the method steps of the computer-implemented method for designing a user-specific writing skill game.

In aspects, a writing device, particularly a smart pen, may be used as input device and output device. In examples, feedback may include game tasks which are projected onto a writing surface, specifically a page, by a pico-projector in the smart pen. In examples, feedback may include game tasks which involve auditory feedback from the smart pen in which the user must create certain notes or tones by completing the required motions. In examples, feedback may include game tasks which rely on haptic feedback from the smart pen in which the user navigates around a virtual 'maze'.

In aspects, a writing device, particularly a smart pen, may be used as input device. In examples, an external device, particularly a display screen or a smartphone, may be used as output device. In examples, the recorded game task performance may be used as user input, particularly as control input, for the writing skill game by transmitting it to the output device. In examples, the recorded game task performance may be transmitted to the output device via an external device interface of the smart pen.

In aspects, an external device, particularly a display screen or a smartphone, may be used as input device and output device. Specifically, the external device may be a touch display screen.

In aspects, after completing the writing skill game, the user may be prompted to practice writing characters which require the use of the handwriting skills which were incorporated in the game tasks of the writing skill game. In examples, the user may be prompted to practice writing characters which require the use the problem areas of the handwriting skills. Thereby the "lesson" of the writing skill game may be reinforced.

The present disclosure further relates to a system for practicing handwriting via a user-specific writing skill game. The system comprises a user input tracking system, a handwriting digitization system, a game design system, a user feedback system, and a handwriting database. The user input tracking system is configured to track a handwriting performance performed by a user with a writing instrument. Particularly, the writing instrument may be a smart pen. The handwriting digitization system is configured to generate a digital representation of the handwriting performance. The game design system is configured to design a writing skill game based on the digital representation of the handwriting performance.

In aspects, the system may be configured to perform the computer-implemented method for designing a user-specific writing skill game.

In aspects, the system may be configured to perform the computer-implemented method for practicing handwriting via a user-specific writing skill game.

In aspects, the user input tracking system may comprise one or more sensors. The one or more sensors may be configured to track a handwriting performance performed by a user. The one or more sensors may be configured to capture input data from the tracked handwriting performance. In examples, the one or more sensors may be configured to track the handwriting performance via motion capture. In examples, the input data may include force data and/or motion data. In examples, the one or more sensors may comprise one or more accelerometers. In examples, the one or more sensors may comprise one or more gyroscopes. In examples, the one or more sensors may comprise one or more magnetometers. In examples, the one or more sensors may comprise one or more optical motion sensors. In examples, the one or more sensors may comprise one or more position sensors. In examples, the one or more sensors may comprise one or more user-oriented sensors, particularly eye tracking sensors. In examples, other additional force, motion, and position sensors known in the art may be comprised by the one or more sensors.

In aspects, the handwriting digitization system may be configured to generate a digital representation of the handwriting performance by calculating from the input data written characters produced by the user and associated user techniques. In examples, the handwriting digitization system may be configured to apply a handwriting calculation algorithm for the generation of the digital representation of the handwriting performance. In examples, the handwriting digitization system may be configured to apply trajectory recognition, character recognition and/or other suitable algorithms which are configured to calculate the written characters from the force and motion data.

In aspects, the user feedback system may be configured to provide the user with game input and/or feedback. In examples, the user feedback system may comprise haptic feedback mechanisms, optical feedback mechanisms and/or audible feedback mechanisms. In examples, haptic feedback mechanisms may comprise one or more vibration motors. In examples, optical feedback mechanisms may comprise one or more projected light source, e.g. one or more pico-projectors. In examples, optical feedback mechanisms may comprise one or more structured light sources. In examples, audible feedback mechanisms may comprise one or more loudspeakers.

In aspects, the game design system may comprise an ideal techniques database storing a set of ideal characters. The ideal characters may comprise ideal writing instrument tip paths and/or ideal techniques. In examples, the game design system may comprise a handwriting skill extraction algorithm configured to determine user-specific handwriting skills. In examples, the game design system may comprise a game design engine. In examples, the game design system may comprise an output system. In examples, the ideal techniques database may store ideal characters, e.g. ideal writing instrument tip paths, linked with ideal techniques to create them. The ideal techniques may comprise expert ideal techniques, specifically fluency information, expert gaze behavior and/or expert motion data. In examples, the output system may be configured to communicate the writing skill game to the writing instrument. In examples, the output system may be configured to communicate the writing skill game to an external device, particularly a smartphone or a display screen. In examples, the output system is configured to calculate user output from the writing skill game, wherein the user output of the writing skill game is communicated. In examples, the output system is a smart pen output system or an external device output system.

In aspects, the system comprises the writing instrument, particularly the smart pen. In examples, the writing instrument may include the user input tracking system and the handwriting digitization system. In examples, the writing instrument may further include the user feedback system. Alternatively, the system may further comprise an external device, particularly a smartphone or a display screen, which includes the user feedback system. In examples, the writing instrument may further comprise an external device interface. In examples, the external device interface may be configured to communicate with the external device. In examples, the external device interface may be configured to communicate with the handwriting database.

DESCRIPTION OF THE DRAWINGS

Other characteristics will be apparent from the accompanying drawings, which form a part of this disclosure. The drawings are intended to further explain the present disclosure and to enable a person skilled in the art to practice it. However, the drawings are intended as non-limiting examples. Common reference numerals on different figures indicate like or similar features.

DETAILED DESCRIPTION

Embodiments of the computer-implemented methods and systems according to the disclosure will be described with reference to the figures as follows.

In the present disclosure, the term "writing skill game" can be understood as an application comprising a set of tasks (in examples only one task). At least one, some or all tasks of the set of tasks may be those tasks (also referred to as game tasks) which require the user to apply the user-specific handwriting skills which are to be improved. That means, in examples, the writing skill game may comprise tasks or sequences which do not require the user to apply the user-specific handwriting skills which are to be improved. The writing skill game or application may be any kind of game, game level, doodle, maze, or other task (or set of tasks) which at least to some extent requires the user to perform elements of motions, directions, ocular-motor skills, eye gaze locations, or other skills or user inputs which form part of the process required to produce handwriting. Because the writing skill game does include at least one game task which require the user to apply the user-specific handwriting skills which are to be improved, the writing skill game may be referred to as user-specific writing skill game.

In the present disclosure, the term "discrete character" can be understood as a character including text elements and/or non-text elements. In examples, discrete characters may be defined as elements which are suitably unique to be associated with a 'correct' user technique. The text elements may, for instance, include letters, signs, and/or glyphs. The non-text elements may, for instance, include geometric shapes and/or patterns.

Figure 1:
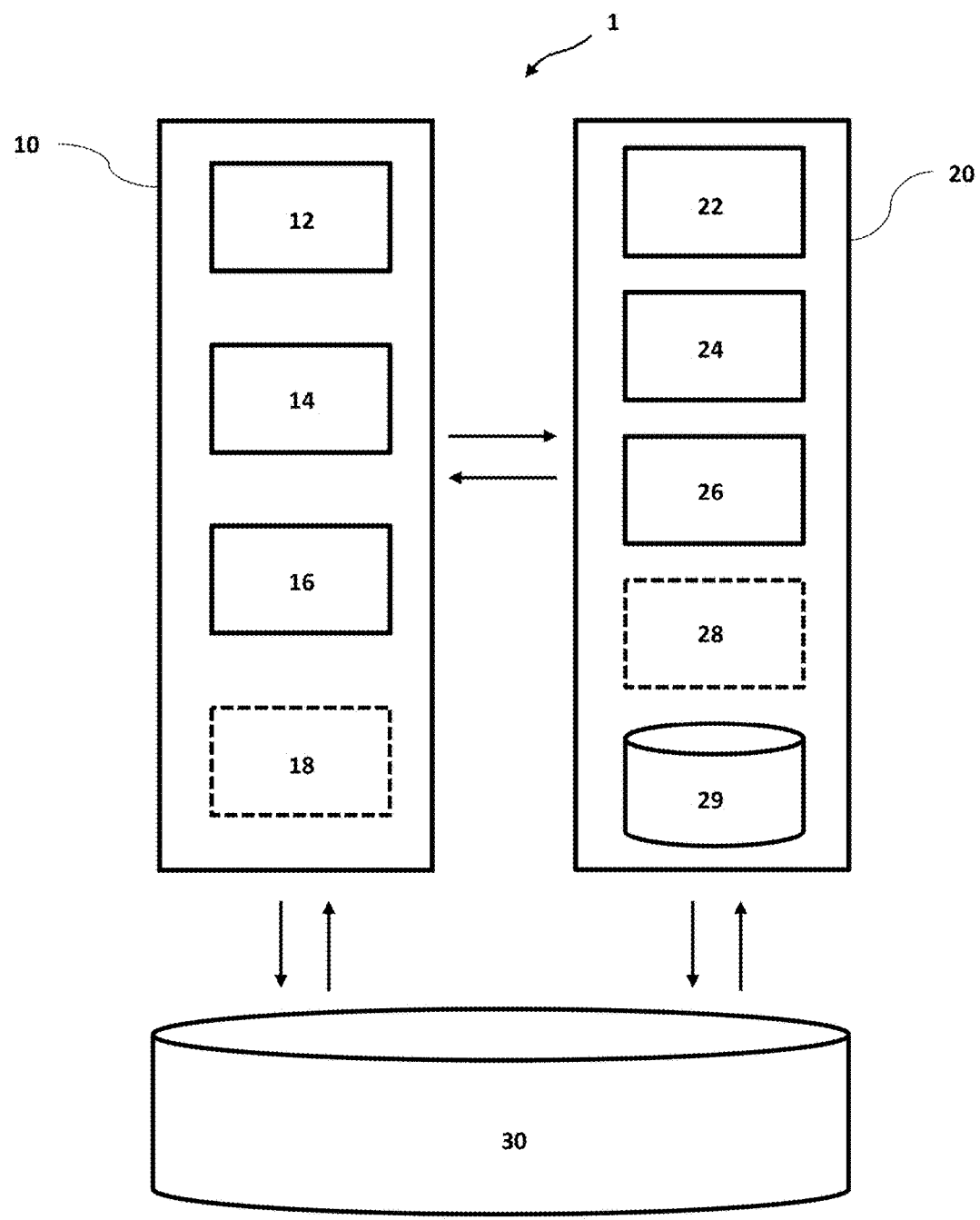
FIG. 1 shows a schematic view of the system for practicing handwriting.
Figure 2:
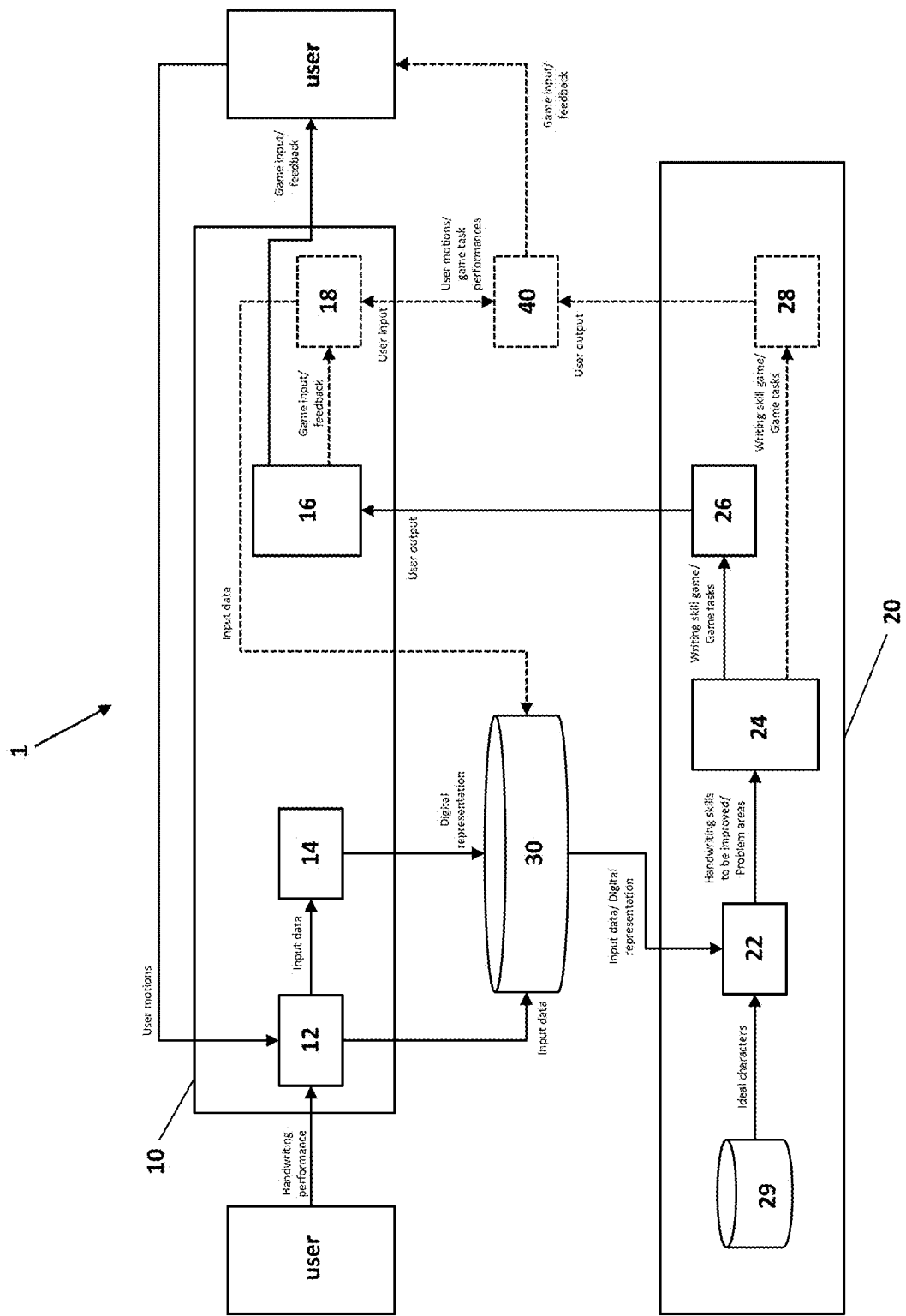
FIG. 2 shows a flow chart of computer-implemented methods carried out by the system.

FIG. 1 is a schematic view of a system 1 for practicing handwriting via a user-specific writing skill game. The system 1 is configured to perform the computer-implemented methods disclosed herein (see, FIG. 2). Specifically, system 1 is configured to perform the computer-implemented method for designing a user-specific writing skill game and the computer-implemented method for practicing handwriting via a user-specific writing skill game.

The system 1 comprises a user input tracking system 12, a handwriting digitization system 14, a game design system 20, a user feedback system 16 and a handwriting database 30. The user input tracking system 12 is configured to track a handwriting performance performed by a user with a writing instrument 10. Particularly, the writing instrument 10 may be a smart pen. The handwriting digitization system 14 is configured to generate a digital representation of the handwriting performance. The game design system 20 is configured to design a writing skill game based on the digital representation of the handwriting performance.

The user input tracking system 12 comprises one or more sensors. The one or more sensors are configured to track a handwriting performance performed by the user. The one or more sensors are configured to capture input data from the tracked handwriting performance. In examples, the one or more sensors are configured to track the handwriting performance via motion capture. The input data may include force data and/or motion data. For instance, the motion data includes motion of the user (e.g. user motion) and/or motion of the writing instrument 10. For instance, the force data includes data regarding the force applied by the user to the writing instrument 10, e.g. gripping force, and/or force applied via the writing instrument 10 to the paper (or other base onto which the handwriting is performed, e.g. a touch display). In examples, the one or more sensors comprise one or more accelerometers. In examples, the one or more sensors comprise one or more gyroscopes. In examples, the one or more sensors comprise one or more magnetometers. In examples, the one or more sensors comprise one or more optical motion sensors. In examples, the one or more sensors comprise one or more position sensors. In examples, the one or more sensors comprise one or more user-oriented sensors, particularly eye tracking sensors. In examples, other additional force, motion and position sensors known in the art are comprised by the one or more sensors. The user input tracking system 12 is configured to store the input data on the handwriting database 30.

The handwriting digitization system 14 is configured to generate a digital representation of the handwriting performance. Therefore, the handwriting digitization system 14 is configured to calculate written characters produced by the user and associated user techniques used for writing the characters. The handwriting digitization system 14 uses the input data for the calculation of the discrete characters and the user techniques. The handwriting digitization system 14 stores the digital representation of the handwriting performance as writing instrument tip path data and user techniques data linked with the writing instrument tip path data in the handwriting database. The handwriting digitization system 14 is configured to apply a handwriting calculation algorithm for the generation of the digital representation of the handwriting performance. In examples, the handwriting digitization system 14 is configured to apply trajectory recognition, character recognition and/or other suitable algorithms which are configured to calculate the written characters, e.g. discrete characters from the force and motion data. In general, the expressions "writing instrument tip path" and "writing instrument tip path data" may also be referred to as "pen tip path" and "pen tip path data", respectively, if a pen, specifically as smart pen is used as writing instrument.

The user feedback system 16 is configured to provide the user with game input and/or feedback. The game input may be the writing skill game, game tasks and/or guides to the writing skill game which can be used by the user. The user feedback system 16 may comprises haptic feedback mechanisms, optical feedback mechanisms and/or audible feedback mechanisms. For instance, the haptic feedback mechanisms may comprise one or more vibration motors. For instance, the optical feedback mechanisms may comprise one or more projected light source, e.g. one or more pico-projectors. For instance, the optical feedback mechanisms comprise one or more structured light sources. For instance, the audible feedback mechanisms comprise one or more loudspeakers. Specifically, the user feedback system may be embodied as a system running on the writing instrument, with access to the feedback mechanism for providing game input and/or feedback. In examples, the user feedback system 16 is configured to directly provide the user with game input and/or feedback. In examples, feedback and/or game input may be delivered to a user via a connection to an external device 40 e.g. a smartphone and use of that device's hardware. The user feedback system 16 may be embodied as software which enables the delivery of feedback and/or game input to a user.

The game design system 20 comprises an ideal techniques database 29, a handwriting skill extraction algorithm 22, a game design engine 24 and an output system 26, 28. The ideal techniques database 29 stores a set of ideal characters.

The ideal characters comprise ideal writing instrument tip paths, e.g. writing instrument tip path data and/or ideal techniques, e.g. ideal techniques data. The ideal techniques may comprise expert ideal techniques, specifically fluency information, expert gaze behavior and/or expert motion data. In other words, the ideal techniques database 29 stores ideal characters, e.g. ideal writing instrument tip paths, linked with ideal techniques to create them. The handwriting skill extraction algorithm 22 is configured to determine user-specific handwriting skills. Therefore, the handwriting skill extraction algorithm 22 is configured to retrieve input data and/or the digital representation of the handwriting performance from the handwriting database 30 and to compare it with ideal characters retrieved from the ideal techniques database 29. The game design engine 24 is configured to design the writing skill game. The game design engine 24 is configured to retrieve the user-specific handwriting skills, specifically problem areas, and to incorporate one or more of the identified problem areas as game tasks into the writing skill game. The output system 26, 28 is a smart pen output system 26 or an external device output system 28. The output system 26, 28 retrieves the writing skill game from the game design engine 24. The output system 26, 28 is configured to communicate the writing skill game to the writing instrument 10 and/or the external device 40. Specifically, the smart pen output system 26 is configured to communicate the writing skill game to the writing instrument 10, e.g. the smart pen. Specifically, the external device output system 28 is configured to communicate the writing skill game to the external device 40. The external device output system 28 is configured to transform user outputs and writing skill games into a format useable by external hardware, such as the external device 40, e.g. a smartphone or display screen or video game systems. The external device 40 may be, for instance a smartphone or a display screen, e.g. a touch screen or other. In examples, the output system 26, 28 is configured to calculate user output from the writing skill game. The output system 26, 28 is further configured to communicate the user output of the writing skill game to the writing instrument 10 and/or an external device 40. The game design system 20 is embodied as software running on an external device, e.g. a smartphone, the writing instrument 10 or in the cloud.

In embodiments, the system 1 comprises the writing instrument 10. The writing instrument 10 specifically is a configured as a smart pen. The writing instrument 10 includes the user input tracking system 12, the handwriting digitization system 14 and the user feedback system 16. In examples, wherein the system 1 comprises the external device 40, particularly a smartphone or a display screen, the external device 40 may include the user feedback system 16. In examples, wherein the system 1 comprises the external device 40, particularly a smartphone or a display screen, the writing instrument 10 may further comprise an external device interface 18. The external device interface 18 is configured to communicate with the external device 40 and with the handwriting database 30. The external device interface 18 is configured to be used as a game input device, e.g. a control device. Therefore, the external device interface 18 may contain suitable processing and communications hardware, e.g. Wi-Fi, Bluetooth or NFC, for transmitting the input data from the user input tracking system to the external device 40. Thereby the external device interface 18 may be used as a game input device with suitably low latency. In examples, the external device interface 18 is configured to transmit the user's motions, e.g. one or more game task performances to the external device 40, which may be used as the control input. In examples, the external device interface 18 is configured to receive inputs from the external device 40 representing haptic or other feedback to display to the user via the user feedback system 16. In examples, the user input tracking system 12 and/or the external device interface 18 is configured to transmit user input used during the performance of the writing skill game to the handwriting database for future use.

Figure 3:
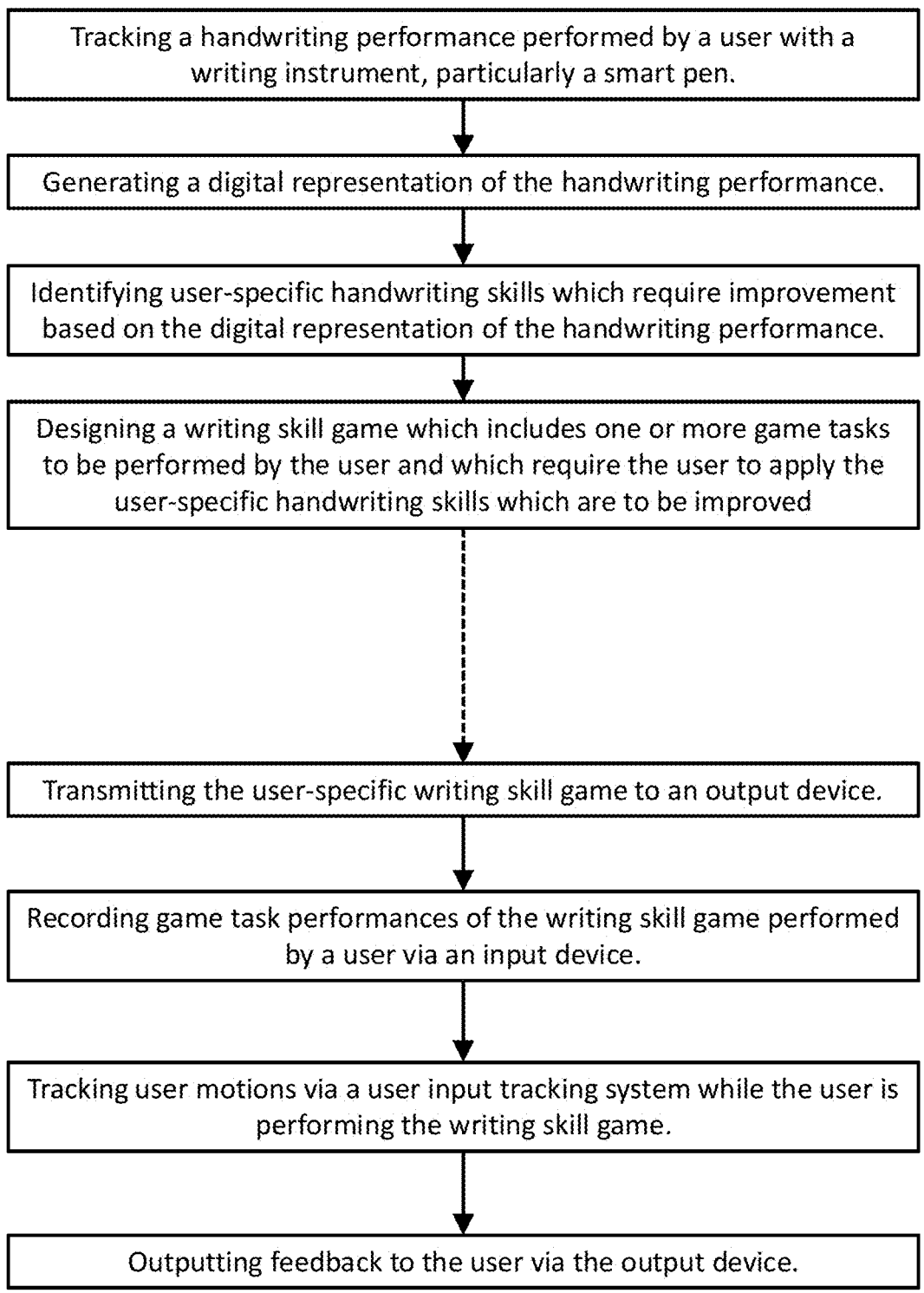
FIG. 3 shows general method steps of the computer-implemented methods.

FIG. 3 depicts the basic steps of the computer-implemented methods disclosed herein. In the top part of FIG. 3, a first method, i.e. a computer-implemented method for designing a user-specific writing skill game is depicted. In the bottom part (separated by the dashed arrow) a follow-on method is depicted which may be perform independently from the first or subsequently to the first method. The second method is a computer-implemented method for practicing handwriting via a user-specific writing skill game. In other words, the method steps depicted in FIG. 3 may be performed subsequently in a single computer-implemented method.

The first method comprises tracking a handwriting performance and generating a digital representation of the handwriting performance. The handwriting performance is performed by a user with the writing instrument 10. Particularly, the writing instrument is a smart pen. After tracking, user-specific handwriting skills which require improvement are identified based on the digital representation of the handwriting performance. Then a writing skill game is designed. The writing skill game is designed to include one or more game tasks to be performed by the user. The one or more game tasks require the user to apply the user-specific handwriting skills which are to be improved.

In examples, the second method may be performed subsequently after the first method, e.g. the second method may include the first method, i.e. one or more of the method steps of the first method (see FIG. 3). For instance, after designing the writing skill game, the user-specific writing skill game is transmitted to the output device. In other words, the user-specific writing skill game is transmitted to an output device is output to the user via the output device. The user may then perform the writing skill game. The game task performances of the user are recorded via an input device. User motions are tracked via the user input tracking system 12 while the user is performing the writing skill game. Feedback to the user is output via the output device. In examples, user motions are tracked analogously to tracking the handwriting performance.

In examples, the second method may be performed independently of the first method. For instance, a user-specific writing skill game may be derived from a writing skill game database, and then the method may be performed as explained above.

In examples, the handwriting performance which is tracked may comprise various pen-based activities. For instance, the handwriting performance may be a writing performance, a drawing performance and/or a marking performance. The expression "pen-based activity" can be understood as an activity for which a 'correct' or optimum output or technique can be defined, and a user's performance towards producing that optimum output can be measured. Handwriting skills include skills and/or procedures which are required for a user to produce handwriting. For instance, the handwriting skills may not include the whole shapes or outlines of written characters, but rather the underlying skills or pen motions required to create written characters. For instance, the handwriting skills include gross and fine motor skills, ocular motor skills and eye gaze behaviour. In embodiments, handwriting skills may include alternatively or additionally other skills, e.g. correct or optimum eye gaze behaviour, hand-eye co-ordination and/or other observable physical motions or behaviours required to produce individual parts of characters or other written features.

Tracking the handwriting performance (and/or the user motion during game task performances) involves capturing via sensors input data of the handwriting performance (and/or the game task performance). The input data includes motion data and/or force data. For instance, the motion data may include motion of the user (e.g. user motion) and/or motion of the writing instrument 10. For instance, the force data may include data regarding the force applied by the user to the writing instrument, e.g. gripping force, and/or force applied via the writing instrument 10 to the paper (or other base onto which the handwriting is performed, e.g. a touch display). The input data is captured via optical sensors. In examples, the input data may be captured via other position tracking techniques.

The input data is used to calculate a writing instrument tip path and user techniques. The writing instrument tip path is calculated based on tracked written characters and/or tracked user motion. The user techniques are calculated based on tracked written characters and/or tracked user motion. The user techniques include, for instance implied forces and/or techniques of the user motion, e.g. start point, end point and/or course of user motion during, e.g. a written character or written word. In examples, the user techniques may include other features of the user's input to the writing instrument. In aspects, the writing instrument tip path may be calculated via dead reckoning using the input data. The user techniques are measured from the input data. Thereby, the user techniques may be acquired by comparing the captured input data with default input data. In examples, the default input data may be input data captured during a handwriting performance of another user, in particular of an expert user. Writing instrument tip path data and user techniques data are generated by storing data representing the writing instrument tip path and user techniques as a function of time, respectively. The writing instrument tip path data and user techniques data are stored in the handwriting database 30. The input data may also be stored in the handwriting database 30.

The digital representation of the handwriting performance is generated by identifying from the writing instrument tip path data discrete characters which are written by the user during the handwriting performance. The identified characters are linked with the user techniques employed to produce them. Each identified character is stored with the respectively linked user techniques in the handwriting database 30. Discrete characters are identified by segmenting the writing instrument tip path data into time-gated periods respectively representing a discrete character. The writing instrument tip path data is segmented by identifying a start and an end of a time-gated period based on one or more of predefined criteria. The predefined criteria comprise, for instance, changes in position or orientation of the writing instrument tip path exceeding a defined threshold, temporal gaps between discrete characters, and/or manual user input. In examples, the predefined criteria may comprise other features of the writing instrument tip path data and/or user techniques data. Specifically, the predefined criteria comprise a combination of some or all of the above-mentioned criteria, e.g. changes in position or orientation of the writing instrument tip path exceeding a defined threshold and temporal gaps between discrete characters.

In examples, the generation of the digital representation of the handwriting performance further include analyzing the writing instrument tip path data over an extended time interval larger than that of one discrete character. During that extended time interval speed and/or accuracy of the handwriting performance can be determined. Specifically, speed and/or accuracy of completing written sentences, written words and/or written characters may be analyzed. The accuracy and the speed of the handwriting performance can be referred to as user fluency level. The writing instrument tip path data and the related user fluency level are stored in the handwriting database 30. The extended time interval may represent one or more words of the handwriting performance, one or more sentences of the handwriting performance and/or the whole handwriting performance.

The identification of user-specific handwriting skills which require improvement may comprise the application of the handwriting skill extraction algorithm 22. The handwriting skill extraction algorithm 22 is configured to analyze the identified characters linked with the user techniques to determine handwriting skills of the user. The handwriting skill extraction algorithm is further configured to identify one or more problem areas of the handwriting skills. These problem areas may be determined as user-specific handwriting skills which require improvement. These problem areas may also later be incorporated in the writing skill game as game tasks. However, it should be understood that, in examples, no problem areas may be identified, but that handwriting skills of the user which are below a minimum threshold of reference handwriting skills may be determined as user-specific handwriting skills which require improvement. These user-specific handwriting skills which require improvement may then afterwards be incorporated in the writing skill game as game tasks.

The handwriting skills of the user are determined based on a comparison of the identified characters with respective ideal characters stored on an ideal techniques database. For instance, the handwriting skills are determined at a character level. The handwriting skills are determined by comparing writing instrument tip path data and user techniques of the identified character with respective data, e.g. ideal writing instrument tip path data and ideal techniques, of the ideal character. Ideal characters and their correlated ideal writing instrument tip path data and ideal techniques may be stored in the ideal techniques database 29. Based on the comparison, handwriting skills used for a respective character may be determined "high" when the respective data of the identified character matches with the ideal character within a defined threshold. Based on the comparison, handwriting skills used for a respective character may be determined "low" when the respective data of the identified character does not match with the ideal character within the defined threshold. Thereby, handwriting skill levels in various handwriting skills may be determined from the user techniques and identified characters. The handwriting skills which are determined "low" may be used as user-specific handwriting skills which require improvement when designing the writing skill game. That means, these one or more of these handwriting skills may be incorporated in the writing skill game as game tasks. Alternatively or additionally, problem areas of the handwriting skills may be determined and incorporated as game tasks in the writing skill game as game tasks as described in more detail below.

In addition or alternatively to determining handwriting skills at a character level, handwriting skills of the user may be determined based on a comparison of the speed of writing motions, the accuracy and/or similarity of repeated characters within the writing instrument tip path of the extended time interval. For instance, the user fluency level may be compared with an ideal fluency level which is stored in the ideal techniques database 29.

Problem areas are identified by detecting a significant difference between the user technique used for an identified character and an ideal technique of an ideal character stored on the ideal techniques database. In examples, the significant difference may be a predefined threshold and/or a predefined constraint. For instance, the significant difference may be determined as the use of an upward stroke (user) technique to form part of a character when the ideal technique would be a downward stroke. Thereby, the handwriting skill extraction algorithm may provide possibilities for ranking and evaluating the handwriting skills which would be most advantageous for the user to practice. In examples, problem areas may be identified by detecting a significant difference between writing instrument tip path data of an identified character and ideal writing instrument tip path data of an ideal character stored on the ideal techniques database. In examples, a problem area of a handwriting skill is calculated based on a deviation of the identified character from the ideal character. For instance, where an identified character is overly 'flattened' while the corresponding ideal characters is rounded, a problem area may be identified in fine motor skills, specifically in rotational fine motor skills. In examples, problem areas may be identified by examining a user fluency level and comparing it to known fluency levels from the ideal techniques database 29. The user fluency level is determined based on relative time to complete the handwriting performance or part of it and the resulting accuracy. Specifically, the user fluency level of the extended time interval may be compared to known fluency levels stored on the ideal techniques database. In examples, identified problem areas may be prioritized. For instance, only a subset, e.g. one or more, of handwriting skills from the problem areas is selected based on the prioritization to be determined as user-specific handwriting skills which require improvement. In examples, the most frequently occurring problem areas identified over several written characters and/or over several handwriting performances may be prioritized.

Designing the writing skill game comprises applying the game design engine 24 configured to design the writing skill game. The game design engine 24 is configured to incorporate one or more of the identified problem areas as game tasks into the writing skill game. Alternatively or additionally, the game design engine 24 is configured to incorporate one or more of the handwriting skills which were determined "low" as game tasks into the writing skill game. The game design engine 24 is further configured to incorporate a positive feedback mechanism into the writing skill game. The positive feedback mechanism is configured to output positive feedback to the user when the game tasks are performed correctly. In examples, writing skill games may be designed with varying lengths and varying required levels of commitment from the user. Thereby short games may be incorporated into small writing breaks while longer games may be played as standalone sessions. In examples, the game design engine 24 may be configured to consider the mental or cognitive workload placed on the user when performing the writing skill game. Thereby an appropriate time to 'prompt' a user to perform the game may be determined.

The writing skill game may be designed from scratch or may be designed by modifying existing games. When designing the writing skill game from scratch pre-existing game level templates are adapted. For instance, the writing skill game is designed by following basic algorithmic game design steps which allow generation of new games following certain patterns. Specifically, the patterns may be mazes or doodles. When modifying existing games, the existing games may be modified such that the writing skill game includes the game tasks which require the user to apply the user-specific handwriting skills which are to be improved. Therefore, the game design engine 24 may contain or access a database of several pre-designed games or parts of games. The game design engine 24 is configured to modify the pre-designed games or parts of games to suit the user-specific handwriting skills. For instance, the game design engine applies generative design algorithms for the modification. The existing games may be video games. The existing games may be games designed specifically for use with the game design engine 24 or unrelated games. Unrelated games may be game whose level features and/or controller mappings are externally modified. In examples, unrelated games may be game whose hardware accepts motion inputs.

Existing games may be modified by modifying the controller input mappings and/or by modifying the level designs of existing games. When modifying the controller input mappings, the game design engine 24 is configured to set an optimum technique to perform an action in the game to match the ideal technique required for the identified problem areas (and/or the one or more handwriting skills which were determined "low"). For instance, when the existing game is a sports game and the action may, for instance, be to throw a ball, the game design engine 24 sets an optimum technique to throw the ball to match the ideal technique, for instance to write the letter C. Modifying the level designs of existing games may for instance, include modifying the level design of racing games. For instance, the game design engine 24 is configured to algorithmically generate course designs for the racing game such that a user completing the course is required to perform user techniques associated with the problem areas (and/or the one or more handwriting skills which were determined "low").

In examples, the writing skill game is designed to comprise game tasks which allow the user to practice motor skills. For instance, the game tasks may be designed to comprise motor skills, e.g. certain ranges of motions, which can be captured via motions of the writing instrument. For instance, a writing skill game may be designed in which a user must rotate the writing instrument in a certain way in order to achieve a task in the writing skill game. This allows a user to practice fine rotational motor skills. The writing skill game may be designed to comprise game tasks which allow the user to practice gaze skills. In examples, this may include achieving an optimized gaze location and/or avoiding undesirable nib fixations. For instance, a writing skill game may be designed in which the user is guided or required to attend to a projected point of light located away from the pen nib, while using the smart pen for providing other game inputs. This may be enhanced by placing game-relevant information on the projected point. In examples, the writing skill game may be designed to comprise game tasks which allow the user to practice the user fluency level. For instance, a writing skill game for practice of fluency level may include solving a maze using the smart pen.

The writing skill game may be designed to comprise game tasks which allow the user to practice various handwriting skills, e.g. one or more different handwriting skills. In examples, the writing skill game may be designed to comprise game tasks which allow the user to practice gross and/or fine motor skills. In examples, the writing skill game may be designed to comprise game tasks which allow the user to practice ocular motor skills. In examples, the writing skill game may be designed to comprise game tasks which allow the user to practice eye gaze behaviour, particularly correct or optimum eye gaze behaviour. In examples, the writing skill game may be designed to comprise game tasks which allow the user to practice hand-eye co-ordination. In examples, the writing skill game may be designed to comprise game tasks which allow the user to practice grip of the smart pen. In examples, the writing skill game may be designed to comprise game tasks which allow the user to practice force or speed of motion. In examples, the writing skill game may be designed to comprise game tasks which allow the user to practice other observable physical motions or behaviours required to produce individual parts of characters or other written features. The writing skill game may be designed to include one or more game tasks which allow the user to practice one or more of the above-mentioned handwriting skills.

The game design engine 24 is configured to determine an appropriate level of difficulty of the writing skill game based on the handwriting skills of the user. For determining the level of difficulty, the game design engine 24 may check the handwriting database 30 for any previous writing skill games the user has played and the handwriting skills and/or problem areas included in those games.

The designed writing skill game is output via the output system 26, 28 which is the smart pen output system 26 or the external device output system 28. Based on the writing skill game user outputs may be calculated by the output system 26, 28. The user outputs may comprise guides to the user enabling the user to play the game. That means in addition to the writing skill game itself guides may be output to the user. In other words, user output may comprise the writing skill game including game tasks and the guides. The guides may include, for instance, haptic feedback, projected light, and/or other guides. In examples, the user outputs may be communicated to an output device. In examples, the output device may be the writing instrument 10 and/or to an external device 40, particularly a smartphone or a display, e.g. a display screen or touch display. In examples, the output system 26, 28 may be configured to transform the writing skill game into a format useable by the external device 40 and/or writing instrument 10 (taking into account the external device's input/output hardware, graphics capabilities, required data structures), and to transmit the correctly formatted writing skill game to the external device 40 and/or writing instrument 10.

When performing the writing skill game, various devices may be used as input device and output device.

For instance, the writing device 10, particularly a smart pen, may be used as input device and output device. The recorded game task performance may be used as user input, particularly as control input, for the writing skill game. The feedback may include game tasks which are projected onto a writing surface, specifically a page, by a pico-projector in the smart pen. In examples, feedback may include game tasks which involve auditory feedback from the smart pen in which the user must create certain notes or tones by completing the required motions. In examples, feedback may include game tasks which rely on haptic feedback from the smart pen in which the user navigates around a virtual 'maze'.

In examples, the writing instrument 10, particularly a smart pen, may be used as input device, and the external device 40, particularly a display screen or a smartphone, may be used as output device. The recorded game task performance may be used as user input, particularly as control input, for the writing skill game by transmitting it to the external device 40 via the external device interface 18.

In examples, the external device 40, particularly a display screen or a smartphone, may be used as input device and output device. Specifically, the external device may be a touch display screen.

After completing the writing skill game, the user may be prompted to practice writing characters which require the use of the handwriting skills which were incorporated in the game tasks of the writing skill game. In examples, the user may be prompted to practice writing characters which require the use the problem areas of the handwriting skills. Thereby the "lesson" of the writing skill game may be reinforced.

Example Method

Figure 4:
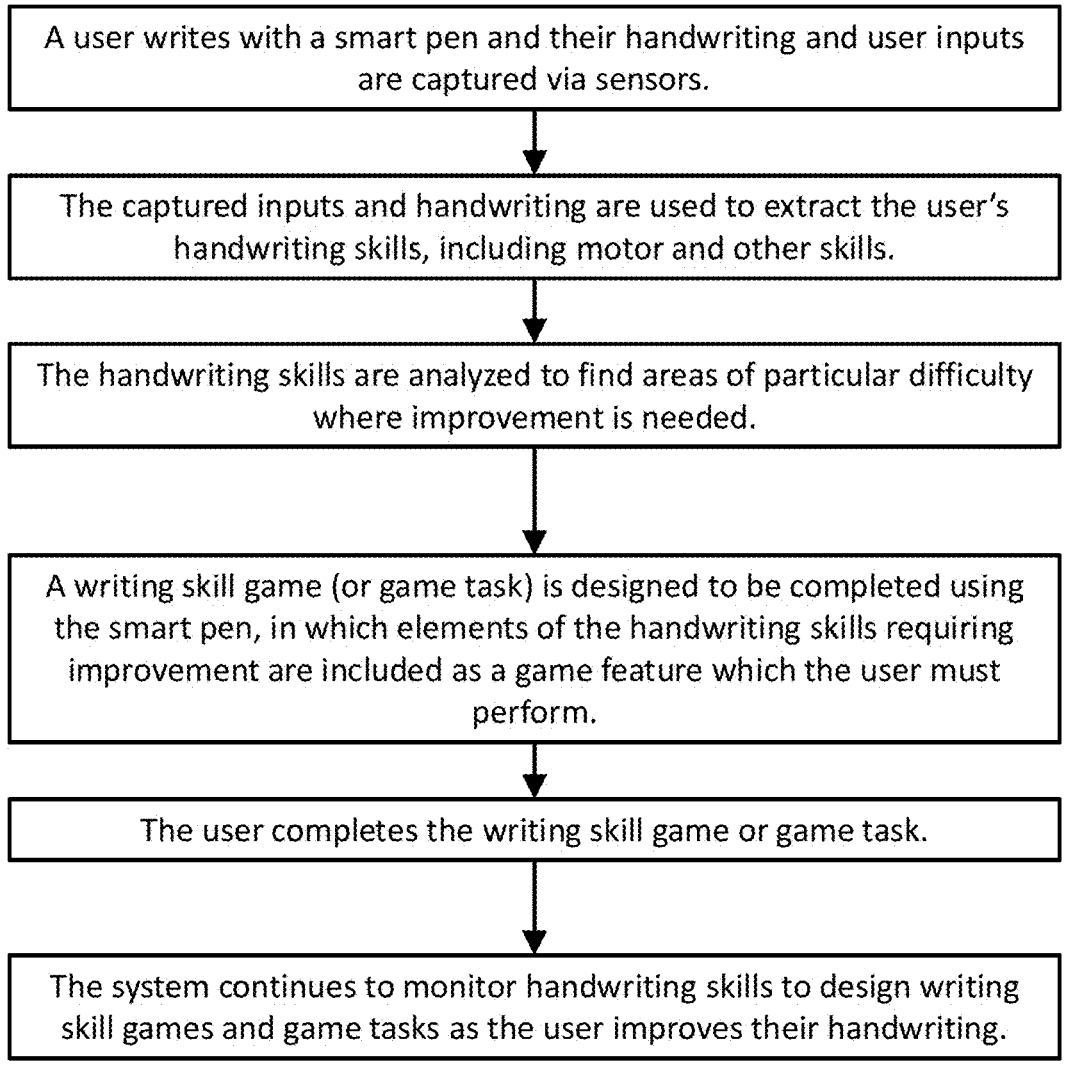
FIG. 4 shows method steps of a first example configuration of the computer-implemented methods.

FIG. 4 depicts a first exemplary configuration of the computer-implemented methods disclosed herein. A user writes with a smart pen and their handwriting and user inputs are captured via sensors. The captured inputs and handwriting are used to extract the user's handwriting skills, including motor and other skills. The handwriting skills are analyzed to find areas of particular difficulty where improvement is needed. A writing skill game (e.g. one or more game tasks) is designed to be completed using the smart pen, in which elements of the handwriting skills requiring improvement are included as a game feature which the user must perform. The user completes the writing skill game or game task. The system continues to monitor handwriting skills to design writing skill games and game tasks as the user improves their handwriting.

Basic Principle

Figure 5:
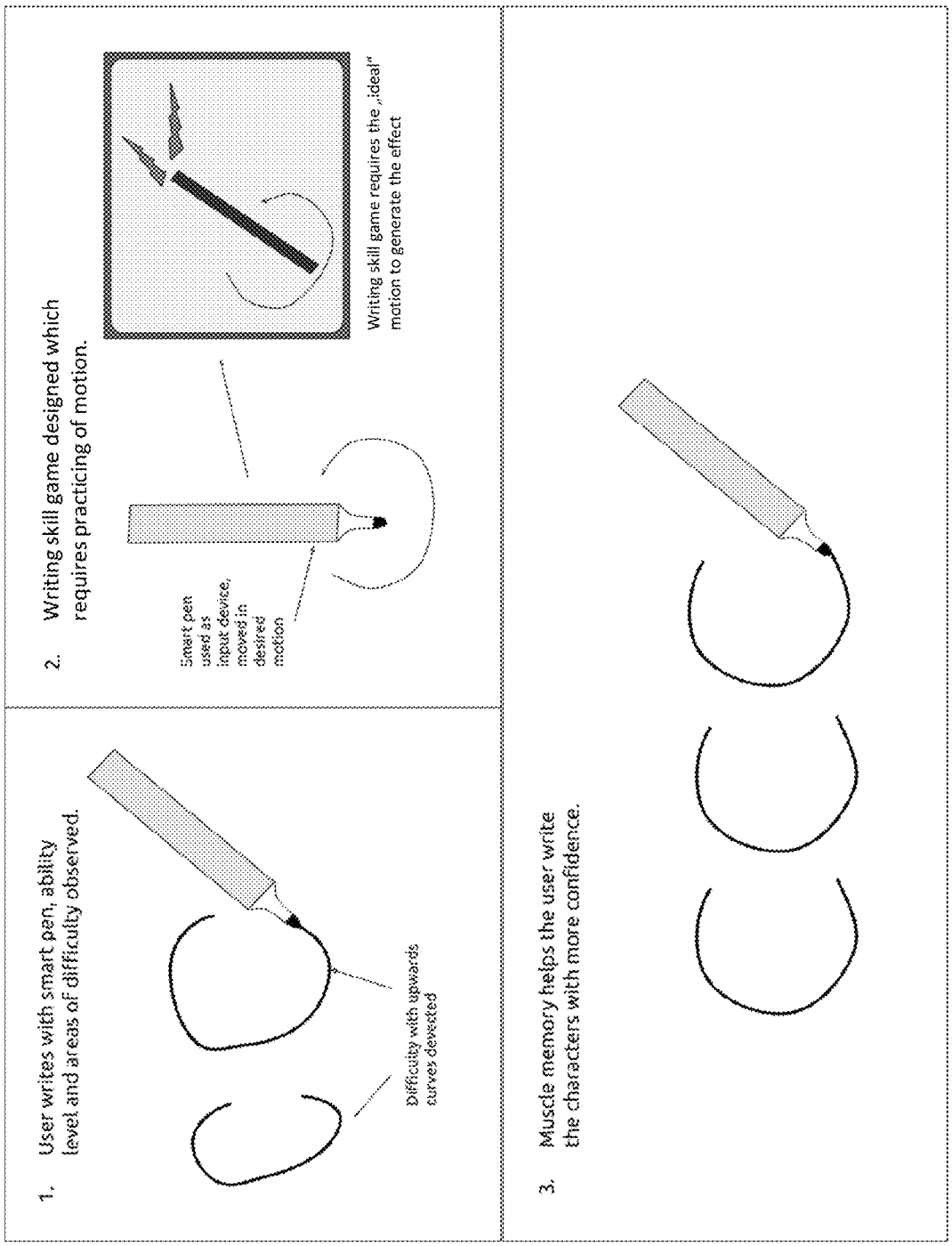
FIG. 5 shows basic principles of the computer-implemented methods.

FIG. 5 schematically depicts the basic principle of the computer-implemented methods. First, a user writes with a smart pen, e.g. a user performs a handwriting performance. During that performance, ability levels and areas of difficulty are observed. In other words, handwriting skills are determined and problem areas are identified. In the example of FIG. 5, difficulties with upward strokes are detected. Then a writing skill game is designed which requires practicing of the motion, which was previously identified as difficulty, i.e. as a user-specific handwriting skill to be improved. That means, the user performs the writing skill game which requires the user to apply the ideal technique, i.e. the ideal motion, to successfully accomplish the writing skill game (or game task), i.e. to generate a correct effect in the writing skill game. The smart pen may thereby be used as an input device for the writing skill game. In other words, the user performs the game tasks with the smart pen as a control device. When having completed the writing skill game, the user may write the characters for which a difficulty was detected previously with more confidence due to muscle memory learned during performing the writing skill game. Thereby, a user can develop, i.e. improve handwriting skills.

It should be understood that the present invention can also (alternatively) be defined in accordance with the following configurations:

1. A computer-implemented method for designing a user-specific writing skill game comprising:
    tracking a handwriting performance performed by a user with a writing instrument, particularly a smart pen,
    generating a digital representation of the handwriting performance, identifying user-specific handwriting skills which require improvement based on the digital representation of the handwriting performance, designing a writing skill game which includes one or more game tasks to be performed by the user and which require the user to apply the user-specific handwriting skills which are to be improved.

2. The computer-implemented method of configuration 1, wherein the handwriting performance comprises a writing performance, a drawing performance, a marking performance and/or any other pen-based activity.

3. The computer-implemented method of any one of the preceding configurations, wherein the handwriting skills include skills and/or procedures which are required for a user to produce handwriting.

4. The computer-implemented method of any one of the preceding configurations, wherein the handwriting skills include one or more of:

gross and/or fine motor skills, ocular motor skills, eye gaze behaviour, particularly correct or optimum eye gaze behaviour, hand-eye co-ordination, and/or other observable physical motions or behaviours required to produce individual parts of characters or other written features.

5. The computer-implemented method of any one of the preceding configurations, wherein tracking the handwriting performance involves capturing via one or more sensors input data of the handwriting performance.

6. The computer-implemented method of configuration 5, wherein the input data is captured via optical sensors.

7. The computer-implemented method of any one of configurations 5 or 6, wherein the input data is used to calculate a writing instrument tip path and user techniques.

8. The computer-implemented method of configuration 7, wherein user techniques include implied forces and/or techniques of the user motion.

9. The computer-implemented method any one of configurations 7 or 8, wherein the writing instrument tip path is calculated via dead reckoning using the input data.

10. The computer-implemented method of any one of configurations 7 to 9, wherein the user techniques are measured from the input data or are acquired by comparing the captured input data with default input data.

11. The computer-implemented method of configuration 10, wherein the default input data is input data captured during a handwriting performance of another user, in particular of an expert user.

12. The computer-implemented method of any one of configurations 7 to 11, wherein writing instrument tip path data and user techniques data is generated by storing data representing the writing instrument tip path and user techniques as a function of time, respectively.

13. The computer-implemented method of any one of configurations 5 to 12, wherein the handwriting performance is tracked via a user input tracking system.

14. The computer-implemented method of any one of the preceding configurations, if at least dependent on configuration 12, wherein generating a digital representation of the handwriting performance includes:

identifying from the writing instrument tip path data discrete characters written by the user during the handwriting performance, linking the identified characters with the user techniques employed to produce them, and storing each identified character with the respectively linked user techniques in a handwriting database.

15. The computer-implemented of configuration 14, wherein discrete characters are identified by segmenting the writing instrument tip path data into time-gated periods respectively representing a discrete character.

16. The computer-implemented of configuration 15, wherein the writing instrument tip path data is segmented by identifying a start and an end of a time-gated period based on one or more of:

changes in position or orientation of the writing instrument tip path exceeding a defined threshold, temporal gaps between discrete characters, manual user input, other features of the writing instrument tip path data or user techniques data.

17. The computer-implemented method of any one of configurations 14 to 16, wherein discrete characters include text elements and/or non-text elements.

18. The computer-implemented method of configuration 17, wherein the text elements include letters, signs, and/or glyphs.

19. The computer-implemented method of any one of configurations 17 or 18, wherein the non-text elements include geometric shapes and/or patterns.

20. The computer-implemented method of any one of configurations 14 to 19, wherein generating a digital representation of the handwriting performance further includes analyzing the writing instrument tip path data over an extended time interval larger than that of one discrete character to determine speed and/or accuracy of the handwriting performance during that extended time interval.

21. The computer-implemented method of configuration 20, wherein the extended time interval represents one or more words of the handwriting performance, one or more sentences of the handwriting performance and/or the whole handwriting performance.

22. The computer-implemented method of any one of the preceding configurations, if at least dependent on configuration 14, wherein identifying user-specific handwriting skills which require improvement comprises applying a handwriting skill extraction algorithm configured to:

analyze the identified characters linked with the user techniques to determine handwriting skills of the user, identify one or more problem areas of the handwriting skills and to determine them as user-specific handwriting skills which require improvement.

23. The computer-implemented method of configuration 22, wherein handwriting skills of the user are determined based on a comparison of the identified characters with respective ideal characters stored on an ideal techniques database.

24. The computer-implemented method of configuration 23, wherein handwriting skills are determined at a character level by:

comparing writing instrument tip path data and user techniques of the identified character with respective data of the ideal character, based on the comparison, handwriting skills used for a respective character are determined "high" when the respective data of the identified character matches with the ideal character within a defined threshold, and "low" when the respective data of the identified character does not match with the ideal character within the defined threshold.

25. The computer-implemented method of any one of configurations 22 to 24, if at least dependent on configuration 20, wherein handwriting skills of the user are determined based on a comparison of the speed of writing motions, the accuracy and/or similarity of repeated characters within the writing instrument tip path of the extended time interval.

26. The computer-implemented method of any one of configurations 22 to 25, wherein problem areas are identified by detecting a significant difference between the user technique used for an identified character and an ideal technique of an ideal character stored on the ideal techniques database.

27. The computer-implemented method of any one of configurations 22 to 26, wherein problem areas are identified by detecting a significant difference between writing instrument tip path data of an identified character and ideal writing instrument tip path data of an ideal character stored on the ideal techniques database.

28. The computer-implemented method of configuration 27, wherein a problem area of handwriting skill is calculated based on a deviation of the identified character from the ideal character.

29. The computer-implemented method of any one of configurations 22 to 28, wherein problem areas are identified by examining a user fluency level and comparing it to known fluency levels from the ideal techniques database.

30. The computer-implemented method of configuration 29, wherein the user fluency level is determined based on relative time to complete the handwriting performance or part of it and the resulting accuracy.

31. The computer-implemented method of any one of configurations 22 to 30, wherein identified problem areas are prioritized and wherein, based on the prioritization, only a subset of handwriting skills from the problem areas is selected to be determined as user-specific handwriting skills which require improvement.

32. The computer-implemented method of configuration 31, wherein the most frequently occurring problem areas identified over several written characters and/or over several handwriting performances are prioritized.

33. The computer-implemented method of any one of the preceding configurations, if at least dependent on configuration 22, wherein designing a writing skill game comprises applying a game design engine configured to design the writing skill game and optionally:
incorporating one or more of the identified problem areas as game tasks into the writing skill game, and/or
incorporating a positive feedback mechanism into the game which is configured to output positive feedback to the user when the game tasks are performed correctly.

34. The computer-implemented method of configuration 33, wherein the writing skill game is designed from scratch by adapting pre-existing game level templates or by following basic algorithmic game design steps which allow generation of new games following certain patterns.

35. The computer-implemented method of configuration 33, wherein the writing skill game is designed by modifying existing games such that the writing skill game includes the game tasks which require the user to apply the user-specific handwriting skills which are to be improved.

36. The computer-implemented method of configuration 35, wherein existing games are modified by modifying the controller input mappings.

37. The computer-implemented method of configuration 36, wherein the game design engine is configured to set an optimum technique to perform an action in the game to match the ideal technique required for the identified problem areas.

38. The computer-implemented method of configuration 35, wherein existing games are modified by modifying the level designs of existing games, particularly racing games.

39. The computer-implemented method of configuration 38, wherein the game design engine is configured to algorithmically generate course designs for the racing game such that a user completing the course is required to perform user techniques associated with the problem areas.

40. The computer-implemented method of any one of the preceding configurations, wherein the writing skill game is designed to comprise game tasks which allow the user to practice motor skills.

41. The computer-implemented method of any one of the preceding configurations, wherein the writing skill game is designed to comprise game tasks which allow the user to practice gaze skills.

42. The computer-implemented method of any one of the preceding configurations, particularly if at least dependent on configuration 12, wherein the writing skill game is designed to comprise game tasks which allow the user to practice the user fluency level.

43. The computer-implemented method of any one of configurations 33 to 42, wherein the writing skill game is designed to comprise game tasks which allow the user to practice one or more of
gross and/or fine motor skills,
ocular motor skills,
eye gaze behaviour, particularly correct or optimum eye gaze behaviour,
hand-eye co-ordination,
grip of the smart pen,
force or speed of motion, and/or
other observable physical motions or behaviours required to produce individual parts of characters or other written features.

44. The computer-implemented method of any one of configurations 33 to 43, wherein the writing skill game design engine is configured to determine an appropriate level of difficulty of the writing skill game based on the handwriting skills of the user.

45. The computer-implemented method of configuration 44, wherein for determining the level of difficulty, the game design engine checks the handwriting database for any previous writing skill games the user has played and the handwriting skills and/or problem areas included in those writing skill games.

46. The computer-implemented method of any one of configurations 33 to 45, wherein the designed writing skill game is output via an output system.

47. The computer-implemented method of configuration 46, wherein the output system is a smart pen output system or an external device output system.
48. The computer-implemented method of any one of configurations 46 or 47, wherein based on the writing skill game user outputs are calculated by the output system.
49. The computer-implemented method of configuration 48, wherein the user outputs comprise guides to the user enabling the user to play the writing skill game.
50. The computer-implemented method of any one of configurations 48 or 49, wherein the user outputs are communicated to the writing instrument and/or to an external device, particularly a smartphone or a display.
51. A computer-implemented method for practicing handwriting via a user-specific writing skill game, the method comprising:
   transmitting a user-specific writing skill game to an output device,
   recording game task performances of the writing skill game performed by a user via an input device,
   tracking user motions via a user input tracking system while the user is performing the writing skill game, and
   outputting feedback to the user via the output device.
52. The computer-implemented method of configuration 51, wherein the writing skill game is designed by the method of any one of configurations 1 to 50.
53. The computer-implemented method of configuration 51 or 52, wherein before transmitting the writing skill game to the output device, the method comprises the method steps of any one of configurations 1 to 50.
54. The computer-implemented method of any one of configurations 51 to 53, wherein a writing device, particularly a smart pen, is used as input device and output device.
55. The computer-implemented method of configuration 54, wherein feedback includes one or more of:
   game tasks which are projected onto a writing surface, specifically a page, by a pico-projector in the smart pen,
   game tasks which involve auditory feedback from the smart pen in which the user must create certain notes or tones by completing the required motions,
   game tasks which rely on haptic feedback from the smart pen in which the user navigates around a virtual 'maze'.
56. The computer-implemented method of any one of configurations 51 to 53, wherein a writing device, particularly a smart pen, is used as input device and an external device, particularly a display screen or a smartphone, is used as output device.
57. The computer-implemented method of configuration 56, wherein the recorded game task performance is used as user input, particularly as control input, for the writing skill game by transmitting it to the output device.
58. The computer-implemented method of configuration 57, wherein the recorded game task performance is transmitted to the output device via an external device interface of the smart pen.
59. The computer-implemented method of any one of configurations 51 to 53, wherein an external device, particularly a display screen or a smartphone, is used as input device and output device.
60. The computer-implemented method of any one of configurations 51 to 59, wherein after completing the writing skill game, the user is prompted to practice writing characters which require the use of the handwriting skills which were incorporated in the game tasks of the writing skill game.
61. A system (1) for practicing handwriting via a user-specific writing skill game comprising:
   a user input tracking system (12) configured to track a handwriting performance performed by a user with a writing instrument (10), particularly a smart pen,
   a handwriting digitization system (14) configured to generate a digital representation of the handwriting performance,
   a game design system (20) configured to design a writing skill game based on the digital representation of the handwriting performance,
   a user feedback system (16), and
   a handwriting database (30).
62. The system (1) of configuration 61 being configured to perform the method of any one of configurations 1 to 60.
63. The system (1) of any one of the preceding configurations, wherein the user input tracking system (12) comprises one or more sensors configured to track a handwriting performance performed by a user and to capture input data from the tracked handwriting performance.
64. The system (1) of configuration 63, wherein the input data includes force data and/or motion data.
65. The system (1) of any one of configurations 63 or 64, wherein the one or more sensors comprise one or more of:
   an accelerometer,
   a gyroscope,
   a magnetometer,
   an optical motion sensor,
   a position sensor, and/or
   a user-oriented sensor, particularly an eye tracking sensor.
66. The system (1) of any one of the preceding configurations, wherein the handwriting digitization system (14) is configured to generate a digital representation of the handwriting performance by calculating from the input data written characters produced by the user and associated user techniques.
67. The system (1) of configuration 66, wherein the handwriting digitization system (14) is configured to apply a handwriting calculation algorithm for the generation of the digital representation of the handwriting performance.
68. The system (1) of any one of the preceding configurations, wherein the user feedback system (16) is configured to provide the user with game input and/or feedback.
69. The system (1) of configuration 68, wherein the user feedback system (16) comprises haptic feedback mechanisms, optical feedback mechanisms and/or audible feedback mechanisms.
70. The system (1) of any one of the preceding configurations, wherein the game design system (20) comprises:
   an ideal techniques database (29) storing a set of ideal characters,
   a handwriting skill extraction algorithm (22) configured to determine user-specific handwriting skills,
   a game design engine (24), and
   an output system (26, 28).

71. The system (1) of configuration 70, wherein the ideal techniques database (29) stores ideal characters linked with ideal techniques to create them, particularly expert ideal techniques, specifically fluency information, expert gaze behavior and/or expert motion data.

72. The system (1) of any one of configurations 70 or 71, wherein the output system (26, 28) is configured to communicate the writing skill game to the writing instrument (10) and/or an external device (40), particularly a smartphone or a display screen.

73. The system (1) of any one of the preceding configurations comprising the writing instrument (10), particularly a smart pen, which includes the user input tracking system (12) and the handwriting digitization system (14).

74. The system (1) of configuration 73, wherein the writing instrument (10) further includes the user feedback system (16).

75. The system (1) of configuration 73 further comprising an external device (40), particularly a smartphone or a display screen, which includes the user feedback system (16).

76. The system (1) of configuration 75, wherein the writing instrument (10) further comprises an external device interface (18) configured to communicate with the external device (40) and/or with the handwriting database (30).

The invention claimed is:

1. A computer-implemented method for designing a user-specific writing skill game comprising:
   tracking a handwriting performance performed by a user with an input instrument;
   generating a digital representation of the handwriting performance;
   identifying user-specific handwriting skills which require improvement based on the digital representation of the handwriting performance;
   designing a writing skill game which includes one or more game tasks to be performed by the user and which require the user to apply the user-specific handwriting skills which are to be improved; and
   outputting feedback to the user via an output instrument, wherein the feedback includes the one or more game tasks projected onto a writing surface by a pico-projector in a writing instrument, and wherein the writing instrument is the input instrument and the output instrument.

2. The computer-implemented method of claim 1, wherein tracking the handwriting performance involves capturing via one or more sensors input data of the handwriting performance.

3. The computer-implemented method of claim 2, wherein the input data is used to calculate a writing instrument tip path and user techniques.

4. The computer-implemented method of claim 3, wherein writing instrument tip path data and user techniques data is generated by storing data representing the writing instrument tip path and the user techniques as a function of time, respectively.

5. The computer-implemented method of claim 4, wherein generating the digital representation of the handwriting performance includes:
   identifying from the writing instrument tip path data one or more discrete characters written by the user during the handwriting performance;
   linking the identified discrete characters with the user techniques employed to produce the identified discrete characters; and
   storing each identified character with a respectively linked user technique in a handwriting database.

6. The computer-implemented method of claim 5, wherein identifying the user-specific handwriting skills which require improvement comprises applying a handwriting skill extraction algorithm configured to:
   analyze the identified characters linked with the user techniques to determine handwriting skills of the user; and
   identify one or more problem areas of the handwriting skills and determine which user-specific handwriting skills correspond to the one or more problem areas which require improvement.

7. The computer-implemented method of claim 6, wherein the handwriting skills of the user are determined based on a comparison of the identified characters with respective ideal characters stored on an ideal techniques database.

8. The computer-implemented method of claim 1, wherein the designing of the writing skill game comprises applying a game design engine configured to design the writing skill game.

9. The computer-implemented method of claim 1, wherein the writing skill game is designed to comprise game tasks which allow the user to practice motor skills.

10. The computer-implemented method of claim 1, wherein the writing skill game is designed to comprise game tasks which allow the user to practice gaze skills.

11. A computer-implemented method for practicing handwriting via a user-specific writing skill game, the method comprising:
    designing the user-specific writing skill game which includes one or more game tasks to be performed by a user and which require the user to apply user-specific handwriting skills which are to be improved;
    transmitting the user-specific writing skill game to an output device;
    recording game task performances of the user-specific writing skill game performed by the user via an input device, wherein a writing device is used as the input device and the output device;
    tracking user motions via a user input tracking system while the user is performing the user-specific writing skill game; and
    outputting feedback to the user via the output device, wherein the feedback includes the one or more game tasks which are projected onto a writing surface by a pico-projector in the writing device.

12. The computer-implemented method of claim 11, wherein the feedback further includes one or more of:
    game tasks which involve auditory feedback from a smart pen in which the user must create certain notes or tones by completing required motions;
    game tasks which rely on haptic feedback from the smart pen in which the user navigates around a virtual 'maze'.

13. The computer-implemented method of claim 11, wherein an external device is used as the output device, and wherein the recorded game task performance is used as user input for the writing skill game by transmitting it to the output device.

14. The computer-implemented method of claim 13, wherein the recorded game task performance is transmitted to the output device via an external device interface of the writing device.

15. The computer-implemented method of claim 12, wherein after completing the writing skill game, the user is prompted to practice writing characters which require the use of the handwriting skills which were incorporated in the game tasks of the writing skill game.

16. A system for practicing handwriting via a user-specific writing skill game comprising:
- a user input tracking system configured to track a handwriting performance performed by a user with a writing instrument;
- a handwriting digitization system configured to generate a digital representation of the handwriting performance;
- a game design system configured to design a writing skill game based on the digital representation of the handwriting performance, wherein the writing skill game includes one or more game tasks to be performed by the user and which require the user to apply user-specific handwriting skills which are to be improved;
- a user feedback system configured to output feedback to the user via an output device, wherein the feedback includes game tasks projected onto a writing surface by a pico-projector in the writing instrument; and
- a handwriting database.

17. The system of claim 16, wherein the user input tracking system comprises one or more sensors configured to track the handwriting performance performed by the user and to capture input data from the tracked handwriting performance, and wherein the input data includes force data and/or motion data.

18. The system of claim 17, wherein the one or more sensors comprise one or more of:
- an accelerometer;
- a gyroscope;
- a magnetometer;
- an optical motion sensor;
- a position sensor; and/or
- a user-oriented sensor, particularly an eye tracking sensor.

19. The system of claim 16, wherein the handwriting digitization system is configured to generate the digital representation of the handwriting performance by calculating from input data written characters produced by the user and associated user techniques.

20. The computer-implemented method of claim 6, wherein identifying the one or more problem areas of the handwriting skills, comprises:
- detecting differences between a technique of the user for an identified character and an ideal technique for respective ideal character stored in an ideal techniques database;
- incorporating, via a game design engine, the one or more problem areas as the one or more game tasks into the writing skill game; and
- incorporating, via the game design engine, a positive feedback mechanism into the writing skill game to output positive feedback to the user when the one or more game tasks are performed correctly.

* * * * *